United States Patent
LaMarca, II et al.

(10) Patent No.: US 11,819,414 B2
(45) Date of Patent: Nov. 21, 2023

(54) PROSTHETIC DEVICES FOR A DECEASED HUMAN BODY AND METHODS OF USE THEREOF

(71) Applicant: LDI Solutions, LLC, Portsmouth, NH (US)

(72) Inventors: Louis J. LaMarca, II, Alton Bay, NH (US); Kraig Markland, Gallatin, TN (US)

(73) Assignee: LDI SOLUTIONS, LLC, Portsmouth, NH (US)

( * ) Notice: Subject to any disclaimer, the term of this patent is extended or adjusted under 35 U.S.C. 154(b) by 263 days.

(21) Appl. No.: 17/503,983

(22) Filed: Oct. 18, 2021

(65) Prior Publication Data

US 2022/0117740 A1  Apr. 21, 2022

Related U.S. Application Data

(60) Provisional application No. 63/092,913, filed on Oct. 16, 2020.

(51) Int. Cl.
*A61F 2/28* (2006.01)

(52) U.S. Cl.
CPC ................ *A61F 2/2857* (2013.01)

(58) Field of Classification Search
CPC ........... A61F 2/2857; A61F 2210/0076; A61F 2230/0069; A61F 2/28; A61F 2/30; A61F 2/50; A61F 2/54; A61F 2/60; A61G 17/044; A61G 17/04
See application file for complete search history.

(56) References Cited

U.S. PATENT DOCUMENTS

2009/0064474 A1\*  3/2009  Dancer ................ A61F 2/2857
27/21.1

\* cited by examiner

*Primary Examiner* — George J Ulsh
*Assistant Examiner* — Erin A Kim
(74) *Attorney, Agent, or Firm* — Grossman, Tucker, Perreault & Pfleger PLLC; Steven J. Grossman

(57) ABSTRACT

The present invention relates to the field of artificial prosthetic devices, which may more particularly be a bone replacement prosthesis, to be particularly disposed on or within, or otherwise used with, a deceased human body (e.g. corpse, cadaver).

10 Claims, 4 Drawing Sheets

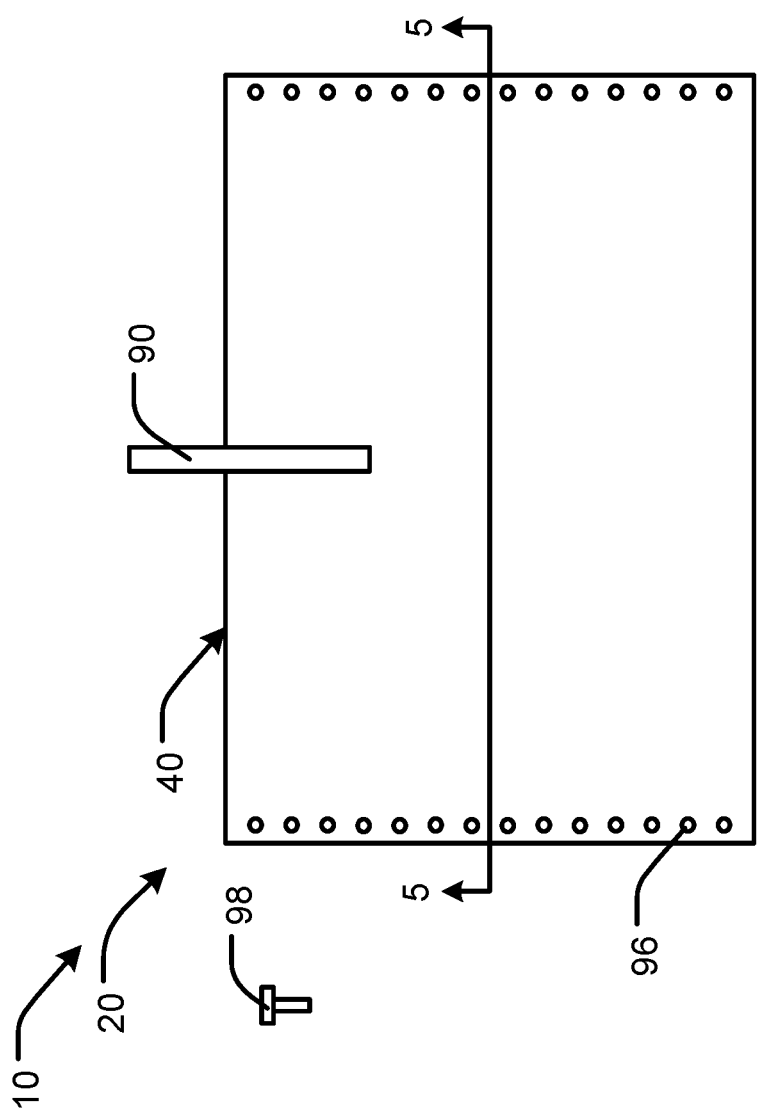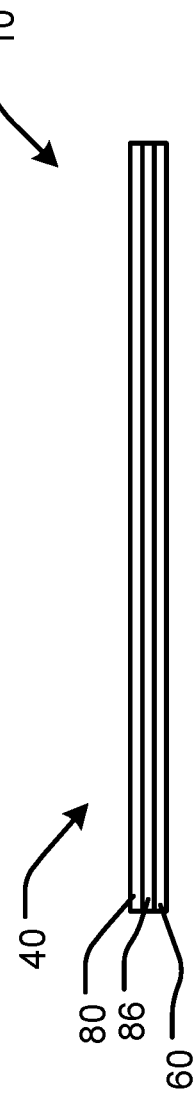
FIG. 4
FIG. 5

PROSTHETIC DEVICES FOR A DECEASED HUMAN BODY AND METHODS OF USE THEREOF

CROSS-REFERENCE TO RELATED APPLICATION

This application claims the benefit of U.S. provisional patent application No. 63/092,913, filed Oct. 16, 2020, the entire disclosure of which is incorporated herein by reference.

FIELD

The present relates to the field of artificial prosthetic devices, which may more particularly be a bone replacement prosthesis, to be particularly disposed on or within, or otherwise used with, a deceased human body (e.g. corpse, cadaver). Such may be utilized, for example, particularly when presenting the deceased human body, such as in an open funerary box (e.g. coffin, casket), at a wake, funeral or other ceremony connected with the final disposition (e.g. burial, cremation) of the body. Such may also be utilized, for example, to support a region of the deceased human body where an originem organ, hard tissue (e.g. bone) or other tissue has been removed from the body for a medical purpose (e.g. organ or other tissue recovery for a bank). Such may also be utilized, for example, when a region the body may require some restoration (e.g. cossetting) by a mortician, embalmer or other person, such as due to the body suffering traumatic perimortem injures.

BACKGROUND

When an organ donor dies, hard tissue (e.g. bones) and soft tissue (e.g. organs) may be removed from the deceased body and processed for use to treat living individuals/people who are in need of (allograft) transplants. However, a problem may occur when bones are removed from the deceased body, particularly in that the body (e.g. soft tissue) may no longer be properly supported in the region where the bones have been removed. As a result of the removal of the bone support structure, it may not be possible to display the deceased body for viewing at a ceremony connected with the final disposition.

In light of a need to replace a bone structure removed from a deceased body, there are a number of bone replacement products on the market, however, each have associated problems.

Artificial bone may be formed of rigid polyvinyl chloride (PVC and referred to as "PVC bone", which may be PVC pipe that is cut to assorted sizes. However, PVC bones from PVC pipe are relatively stiff, which makes such difficult to bend for use in a deceased body. Furthermore, adjusting their size is performed through a complex system of holes and pegs, and securing hardware may be difficult to use. Moreover, tooling costs for injection molding or extrusion of PVC bone may be expensive. As a result, PVC bone may be understood to be expensive, and attachment to the residual skeletal structure may be difficult and sometimes ineffective.

Another problem associated with the use of PVC bone is that it may produce undesirable residual by-products when it is burned in a cremator (also known as a crematory, retort or cremation chamber). These residual by-products may include hydrochloric acid ("HCl"), which may gum up and otherwise damage the cremator. PVC incineration by-products may also emit hazardous emissions into the atmosphere, such as chlorobenzenes and dioxins. In light of the foregoing, some states require that PVC bones be removed prior to cremation, which adds handling, time and cost to final disposition ceremonies.

Another problem associated with the use of PVC bone is that some "green" cemeteries may require removal of PVC bone prior to burial, as hazardous materials in the PVC, such as chlorine monomer and heavy metals may leach into ground water.

Artificial bone may also be formed of corn based polylactic acid (PLA), which may be referred to as "PLA bone". Similar to PVC bone, PLA bone is relatively stiff, which makes such difficult to bend for use in a deceased body. Also similar to PVC bone, adjusting the size of PLA bone is performed through a complex system of holes and pegs, and securing hardware may be difficult to use. PLA bone is generally more expensive than PVC bone, but does not have the hazards associated with incineration or burial.

Artificial bone may also be formed of wood. However, the processes to make wood bone is complex and time consuming, and once again, adjusting size is done through a complex system of holes and pegs. Similar to PVC bone and PLA bone, wood bone is relatively stiff, which makes such difficult to bend for use in a deceased body. Moreover, attachment to the residual skeletal structure may be difficult and sometimes ineffective and the products are relatively expensive.

In light of the foregoing, it may be understood that current artificial bone replacements do not adequately restore the normal anatomical body appearance or appendage (extremity) stability. Furthermore, restoration is dependent on adding additional bulking or absorbent materials by the restoration person(s) (e.g. mortician, embalmer). Moreover, even with these materials, the desired pose of the deceased body may be unstable (e.g. hands may be freely moveable if touched). In such regards, transport from the restoration location to a viewing location is a concern.

Beyond the foregoing, the present artificial bones may provide an unnatural appearance (e.g. arm, forearm and wrist appear emaciated due to volume loss; bulk filling materials may give a unnatural "bumpy or lumpy" appearance; bulk filling materials do not "feel" natural when felt or palpated) and/or an unnatural pose (e.g. hands and fingers may not stay in preferred resting pose; wrist is not stable and can move freely; elbow does not bend or naturally). As such, adjustment requires use of screws, wire or wooden pins may give rise to a sharps injury to the restoration person.

In addition, current artificial bone may not address a need for control of embalming fluid leakage, odor, and safety hazards associated with exposure thereto. Current artificial bone requires extensive use of bulk filling or absorbent materials to absorb fluid.

SUMMARY

The present disclosure provides a method of supporting an appendage of a deceased human body, comprising: removing a bone from the appendage of the human body; obtaining a bone replacement prothesis, wherein the bone replacement prothesis comprises a planar panel, wherein the planar panel comprises a plastic sheet and a fluid absorbent textile, and wherein the planar panel is formable into a tubular form; wrapping the planar panel into the tubular form; and supporting the appendage with the tubular form.

The present disclosure provides a method of supporting an appendage of a deceased human body, comprising: removing a bone from the appendage of the human body;

obtaining a bone replacement prothesis, wherein the bone replacement prothesis comprises a planar panel, wherein the planar panel comprises a plastic sheet and a fluid absorbent textile (e.g. fabric), and wherein the planar panel is formable into a tubular form; wrapping the planar panel around an outside of the appendage and into the tubular form; and securing the tubular form around the outside of the appendage.

The present disclosure also provides another method of supporting an appendage of a deceased human body, comprising: removing a bone from the appendage of the human body; obtaining a bone replacement prothesis, wherein the bone replacement prothesis comprises a planar panel, wherein the planar panel comprises a plastic sheet and a fluid absorbent textile, and wherein the planar panel is formable into a tubular form; wrapping the planar panel into the tubular form; and inserting the tubular form into the appendage in a location from which the bone was removed.

The present disclosure provides an artificial prosthetic device for an appendage of a deceased human body, comprising: a bone replacement prothesis; wherein the bone replacement prothesis comprises a planar panel; wherein the planar panel comprises a plastic sheet and a fluid absorbent textile; and wherein the planar panel is formable/formed into a tubular form, wherein the tubular form is configured to extend around the appendage of the body and/or configured to be disposed within the appendage of the body.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein:

FIG. 4 is another plan view of the bone replacement prothesis, in planar form, according to the present disclosure; and FIG. 5 is a cross-sectional side view the bone replacement prothesis of FIG. 4 taken along line 5-5 of FIG. 4.

DETAILED DESCRIPTION

Figure 1:
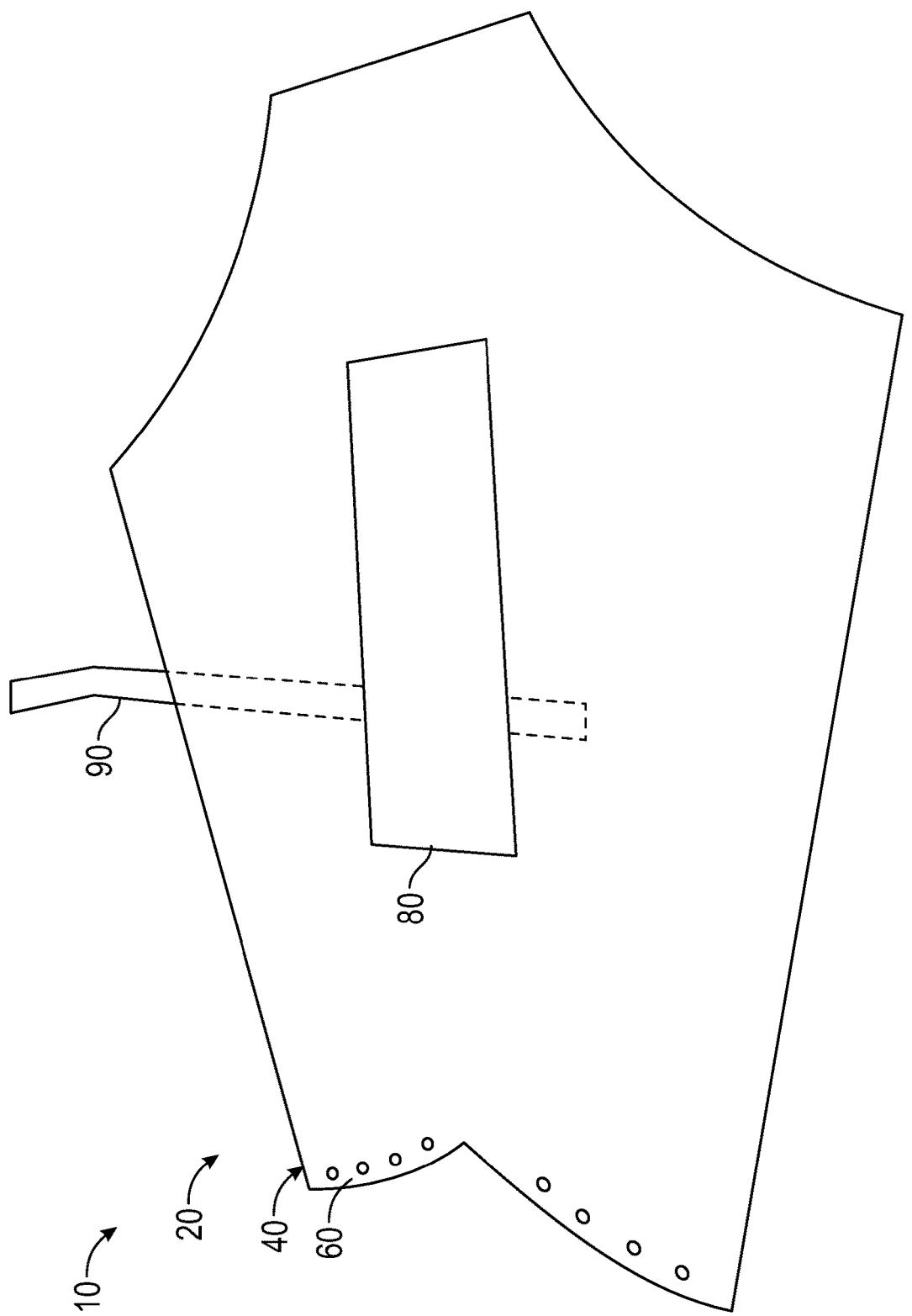
FIG. 1 is a plan view of one embodiment of an artificial prosthetic device, as a bone replacement prothesis, in planar form, according to the present disclosure.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

Referring now to the figures, the present disclosure provides a post-mortem artificial prosthetic device 10 which may comprise a post-mortem bone replacement prothesis 20, particularly configured to support soft tissue of an appendage of a human body, particularly in an absence of one or more supporting (underlying) bones which have been removed from the body, such as for donation to another individual or to an organization. The appendage may include an arm, a leg or any portions thereof.

The bone replacement prothesis 20 may provide a pliable composite laminate structure to support the soft tissue of the appendage of the human body after removal of one or more supporting (underlying) bones therefrom.

As shown in FIG. 1, prior to being applied to a body, the bone replacement prothesis 20 may have a first form of a pliable (bendable), planar, laminate panel 40. Panel 40 may comprise a plastic sheet 60 and a fluid absorbent textile 80 which are laminated to one another to provide a composite laminate. Plastic sheet 60 may comprise one or more extruded, solid, continuous (fluid (air, water) impermeable) plastic layers, which may each comprise a thermoplastic polymer composition comprising one or more polymers.

The plastic sheet 60 may have a thickness in a range of 0.010 inch to 0.070 inch, more particularly 0.015 inch to 0.060 inch, and even more particularly 0.02 inch to 0.04 inch, and may be extruded a thermoplastic polymer composition which comprises, essentially consists of, or consists of one or more polymers such as polyolefin (e.g. polyethylene such as high-density polyethylene, polypropylene), acrylonitrile-butadiene-styrene, polystyrene, polymethyl methacrylate, polycarbonate, polyoxymethylene, polyphenylene oxide, polyamide and blends thereof. Preferred thermoplastic polymer compositions may comprise, essentially consist of, or consist of polyolefin (e.g. polyethylene such as high-density polyethylene, polypropylene), and blends thereof, particularly due to low cost.

The plastic sheet 60/polymer composition may have a flexural modulus as measured in accordance with ASTM D-790-10 of at least 80,000-400,000 psi. at room temperature (23° C.) in order for the plastic sheet to provide sufficient rigidity for the applications disclosed. More particularly, the plastic sheet/polymer composition may have a flexural modulus as measured in accordance with ASTM D-790-10 in a range of 100,000-300,000 psi. at 23° C.

Fluid absorbent textile 80 may comprise one or more textile layers, which may be woven, non-woven, knitted fiber layers, including woven, non-woven and knitted fabrics.

The textile may be a woven, non-woven and knitted fabric may be coated, impregnated or otherwise include a composition which neutralizes formaldehyde solution and/or vapor. An exemplary composition may comprise urea. A more particular exemplary composition is disclosed in U.S. Pat. No. 7,825,066 entitled "Rapid formaldehyde neutralization using chemically treated dry materials" in the name of Skaggs et al, the teachings of which are incorporated by reference herein.

The plastic sheet 60 and the fluid absorbent textile 40 may be laminated to one another with an adhesive, such as a pressure sensitive adhesive or via heated (e.g, flame) lamination. The plastic sheet 60 may be PVC-free (i.e. does not contain polyvinyl chloride), while the fluid absorbent textile 40, may abate (e.g. neutralize) the odor of formaldehyde.

Figure 2:
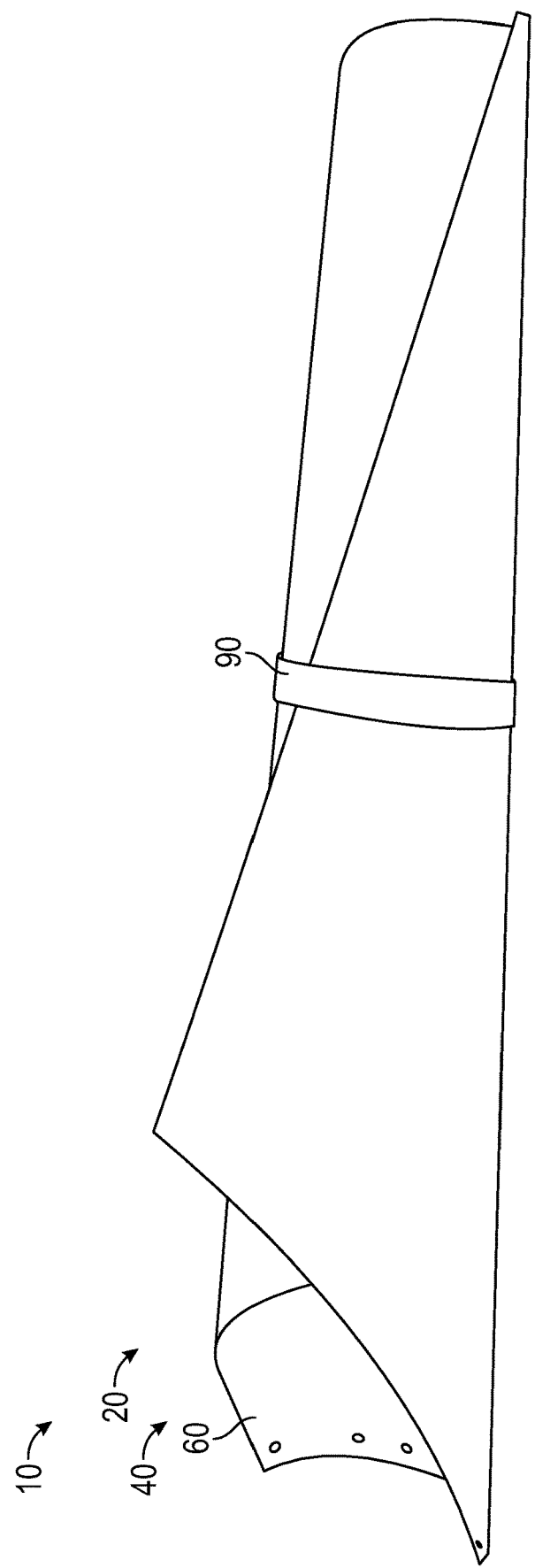
FIG. 2 is a side view of the bone replacement prothesis of FIG. 1 is tubular form.

As shown by FIG. 2, the panel 40 of the bone replacement prothesis 20 may be bent and wrapped around the outside of an appendage (e.g. leg) of a deceased body, particularly where the appendage has had one or more bones removed therefrom and lacks the structural support provided by the removed bone(s). The panel 40 may be wrapped around the soft tissue (e.g. muscle tissue) of the appendage one or more times (one time may be considered one complete loop/coils around the appendage) depending on the requisite support required by the bone replacement prothesis 20. Thus, once applied to a body, the panel 40 may transition from a first planar form to a second tubular form.

Once the panel 40 of bone replacement prothesis 20 may be wrapped around the appendage, the bone replacement prothesis 20 may be retained against unraveling or otherwise loosening by one or more reusable fasteners 90, which may comprise a strap which wraps around at least a portion of a circumference of the tubular form of the prothesis 20, such as a hook and loop fastener (e.g. Velcro brand hook and loop fastener), or other fasteners such as spring clips and/or push pins 98 inserted into holes 96 (see FIG. 4).

The bone replacement prothesis 20 may be secured in place in the tubular form after removal of one or more bones by tissue removal personnel, and then subsequently re-secured (e.g. loosened and readjusted) by restorer personnel. The reusable fastener 90 (as well as 98) allows the bone replacement prothesis 20 to be adjusted to different size diameter appendages and to be easily removed and re-secured. The bone replacement prothesis 20 is arranged such that the inside of the tubular form comprises the fluid absorbent textile 40, which is now arranged adjacent the appendage to abate (e.g. neutralize) the odor of formaldehyde, if the body has been embalmed.

Figure 3:
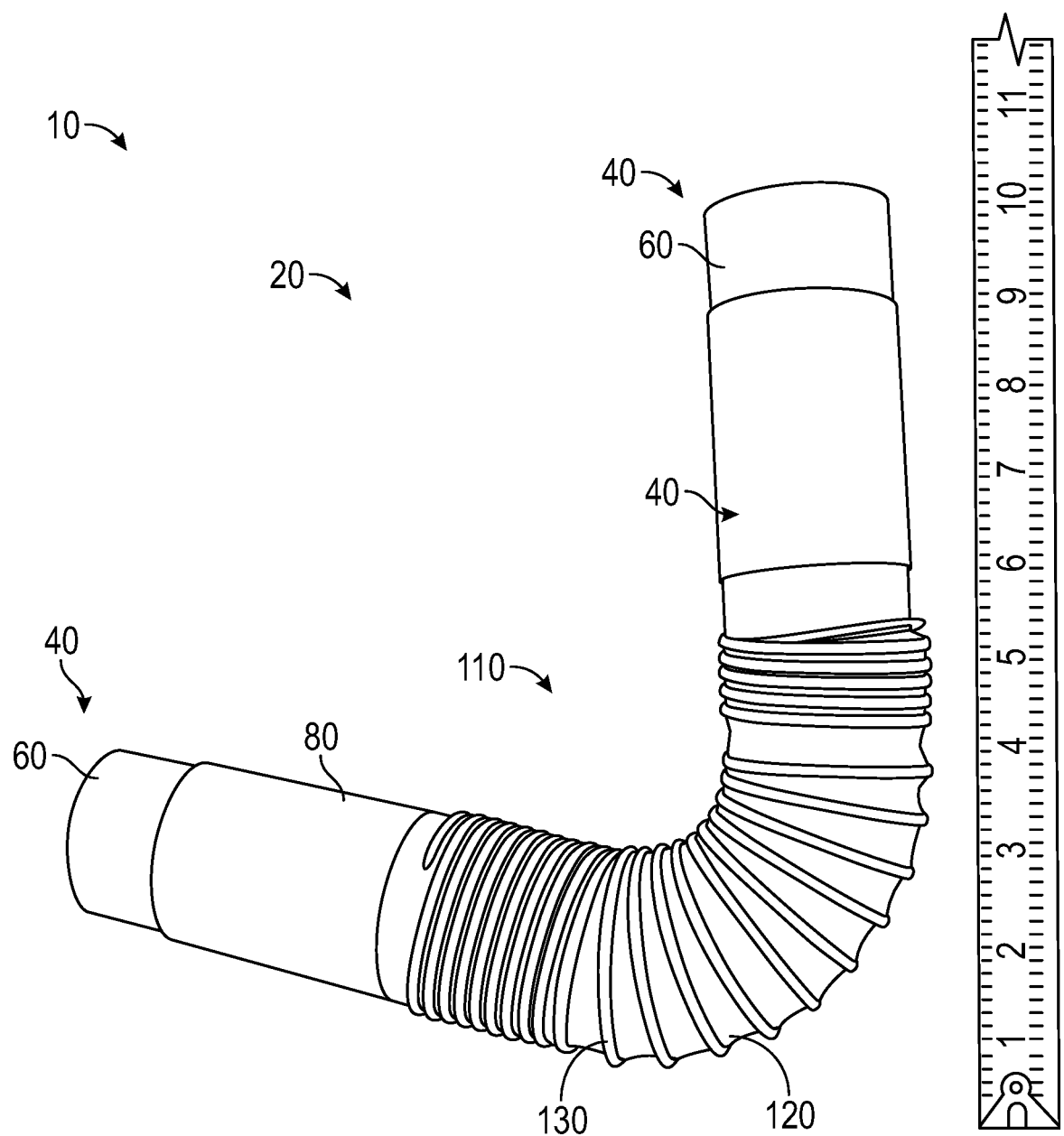
FIG. 3 is a side view of another embodiment of a bone replacement prothesis according to the present disclosure.

In another embodiment as shown in FIG. 3, the artificial prosthetic device 10, and more particularly the bone replacement prothesis 20, may comprises two panels 40 which are transitioned from a planar form into a tubular form, having a diameter of 0.5 inch to 12 inches, and any range therebetween. However, rather than the fluid absorbent textile 40 being disposed around the inside of the tubular form as with the prior embodiment, the fluid absorbent textile 40 is disposed around the outside of the tubular form. The fluid absorbent textile 40 is disposed around the outside of the tubular form particularly as the current embodiment of the artificial prosthetic device 10 is inserted into the appendage, rather than being wrapped around an outside of the appendage as with the first embodiment. As shown, the artificial prosthetic device 10 may be used to replace the humerus, radius and ulna bones of the arm, including the elbow joint.

As shown, the tubular forms of each of the two panels 40 are inserted into opposing open ends of a cylindrical, bendable, extendible, reinforced tube 110. As shown, tube 110 comprises a cylindrical extruded tubing segment 120 disposed within the confines of a cylindrical, helical coil 130. The helical coil 130 may also be disposed as a reinforcement within the extruded tube segment. Tube 110 may be bent into a number of configurations including an elbow (90 degree bend) as shown. More particularly, as shown, the tubular forms of each of the two panels 40 are inserted into opposing open ends of the tubing segment 120, for a length which may be in a range, for example of 0.5 inch to 5 inches. As such, it may be understood that an outside diameter of the tubular form is slightly less than the inside diameter of the tubing segment 130. Thereafter, the artificial prosthetic device 10, and more particularly the bone replacement prothesis 20, may be inserted into an appendage of a deceased human body, and be disposed in a location previously occupied by one or more bones which have been removed from the body.

In light of the foregoing, it may be understood that the bone replacement prothesis 20 is formed from a planar composite structure which provides support while being sufficiently flexible to allow for it to be bent or countered so it may be utilized and provide body reconstruction needs. In addition, the composite has the additional advantage that it can be selectively cut at any location so that it can be segmented as needed, as well as absorb fluids such as embalming and bodily fluids and neutralize odors. In light of such, funeral directors can achieve more naturally pleasing outcomes and restoration and embalmers can reduce restoration timeframes and overall material costs, as well as have reduced exposure to chemicals, blood pathogens or other odors associated with leakage of body and embalming fluids.

The composite structure is also such that it can be readily sized to the desired length without the need to rely upon a peg/hole system noted above. It is strong enough to allow transportation and handling of a deceased human body, yet can be easily bent and adjusted to allow appendages (legs and arms) to be repositioned for casket viewing. Also, there is no need for separate elbow pieces or telescoped tubing to connect the bone segments. Moreover, the composite product herein is made with environmentally more favorable materials vs resins such as PVC and also provides clean burning requirements that are compatible with crematorium requirements.

The foregoing artificial prosthetic device 10, and more particularly the bone replacement prothesis 20 may allow a more normal anatomical positioning and pose while addressing the embalmer's highest technical concerns: leakage and embalming chemical odors. Current available devices do not address the soft tissue volume loss. The device has enough volume to be visually pleasing and provides firmness. The device can be easily modified in length or diameter for specific anatomical or posing needs.

FIG. 4 shows another plan view of the artificial prosthetic device 10 and more particularly the bone replacement prothesis 20, in planar form, while FIG. 5 shows a cross-sectional view of the laminate panel 40, with plastic sheet 60, fluid absorbent textile 80 and pressure sensitive adhesive 86 located therebetween.

Accordingly, the present invention provides a pliable composite structure as a bone replacement structure for deceased human bodies that facilitates the ability to bend, reposition and customize sizing, to realize bone replacement that can be more readily employed by funeral home operators and those associated with organ and tissue bank recovery. The semi-rigid composite is conveniently customizable, meaning that it can be readily configured for a given bone replacement situation and provides the added benefit of restoring both bone and soft tissue. The composite is also environmentally friendly and protects against employee exposure to the odor and hazards of formaldehyde and embalming fluids.

While preferred embodiments of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

LISTING OF REFERENCE CHARACTERS 10 artificial prosthetic device
20 bone replacement prothesis
40 planar panel
60 plastic sheet
80 fluid absorbent textile 86 pressure sensative adhesive
90 fastener
96 hole
98 push pin fastener
110 tube
120 tubing segment

What is claimed is:

1. A method of supporting an appendage of a deceased human body, comprising:
removing a bone from the appendage of the human body;
obtaining a bone replacement prothesis,
   wherein the bone replacement prothesis comprises a planar panel,
   wherein the planar panel comprises a plastic sheet and a fluid absorbent textile, and
   wherein the planar panel is formable into a tubular form;
wrapping the planar panel into the tubular form; and
supporting the appendage with the tubular form.

2. The method of claim 1, further comprising:
inserting the tubular form into the appendage in a location from which the bone was removed.

3. The method of claim 2, wherein:
inserting the tubular form into the appendage in a location from which the bone was removed is performed after wrapping the planar panel into the tubular form.

4. The method of claim 1, further comprising:
securing the planar panel in the tubular form.

5. The method of claim 4, wherein:
securing the planar panel in the tubular form is performed with at least one fastener.

6. The method of claim 5, wherein:
securing the planar panel in the tubular form with at least one fastener is performed after wrapping the planar panel into the tubular form.

7. The method of claim 1, wherein:
the plastic sheet and a fluid absorbent textile are laminated to one another; and/or
the plastic sheet has a thickness in a range of 0.010 inch to 0.070 inch; and/or
the plastic sheet comprises at least one of polyolefin, acrylonitrile-butadiene-styrene or polymethyl methacrylate; and/or
the plastic sheet is free of poly vinyl chloride whereby the sheet does not include poly vinyl chloride.

8. The method of claim 1, further comprising:
wrapping the planar panel around an outside of the appendage.

9. The method of claim 8, further comprising:
securing the tubular form around the outside of the appendage.

10. The method of claim 8, wherein:
securing the tubular form around the outside of the appendage is performed with at least one fastener.

* * * * *